United States Patent
Kawagishi et al.

(10) Patent No.: US 6,582,405 B2
(45) Date of Patent: Jun. 24, 2003

(54) ELECTRICALLY-DRIVEN DENTAL INJECTOR

(75) Inventors: Yukio Kawagishi, deceased, late of Tokyo (JP), by Kayoko Kawagishi, Masayuki Kawagishi, Youko Kawasaki; Kayoko Kawagishi, executor, Machida (JP); Masayuki Kawagishi, executor, Machida (JP); Youko Kawasaki, executor, Machida (JP); Fumio Tanaka, Tokyo (JP); Mutsumi Shibuya, Tokyo (JP); Ikuo Kitagawa, Chiba-Ken (JP); Renji Hayashi, Chiba-Ken (JP); Yoshinori Katoh, Chiba-Ken (JP)

(73) Assignees: Showa Yakuhin Kako Co., Ltd. (JP); Hios Inc. (JP)

( * ) Notice: Subject to any disclaimer, the term of this patent is extended or adjusted under 35 U.S.C. 154(b) by 157 days.

(21) Appl. No.: 09/849,515

(22) Filed: May 7, 2001

(65) Prior Publication Data
US 2002/0077601 A1 Jun. 20, 2002

Related U.S. Application Data

(63) Continuation of application No. PCT/JP00/06044, filed on Sep. 6, 2000.

(30) Foreign Application Priority Data
Sep. 7, 1999 (JP) .......................... 11-252908

(51) Int. Cl.⁷ .............................. A61M 5/00
(52) U.S. Cl. ................ 604/187; 604/208; 604/224; 604/131; 433/114; 433/131
(58) Field of Search .................. 604/224, 15, 16, 604/18, 36, 118, 124, 125, 131, 154, 187, 208, 209, 232; 433/114, 131

(56) References Cited

U.S. PATENT DOCUMENTS
4,602,700 A    7/1986    Szabo

FOREIGN PATENT DOCUMENTS
| | | |
|---|---|---|
| JP | 5-42215 A | 2/1993 |
| JP | 6-7440 A | 1/1994 |
| JP | 6-52838 U | 7/1994 |

*Primary Examiner*—Sharon Kennedy
*Assistant Examiner*—Kathryn L. Thompson
(74) *Attorney, Agent, or Firm*—Nixon Peabody LLP; Donald R. Studebaker

(57) ABSTRACT

An electrically-driven dental injector used in orally injecting such an injection liquid as an anesthetic in dental treatment. Electrically-driven dental injectors includes one having a mechanism for disengaging a pinion (82) from a rack (48) in order to retract a plunger rod (44) upon completion of injection; however, it has heretofore been necessary to manually operate the operating part from outside each time. The inventive electrically-driven dental injector is so arranged that the plunger rod can be manually pushed back directly oupon completion of injection without requiring manual operation, and, to this end, the injector comprises a latch mechanism (84) for engaging/disengaging the ring gear (70) of a planetary reduction gear (50) with/from a casing (52), and an operating rod (94) extending through a support member (20) and functionally cooperating with the latch mechanism (84).

4 Claims, 7 Drawing Sheets

ELECTRICALLY-DRIVEN DENTAL INJECTOR

This application is a continuation of PCT/JP00/06044 filed Sep. 6, 2000.

TECHNICAL FIELD

This invention relates to electrically-driven dental injectors for use in injection of an injection liquid such as an anesthetic into the mouth cavity in dental treatment.

BACKGROUND ART

A cartridge type injector is generally used in injection of the anesthetic in dental treatment. When the anesthetic is injected into the mouth cavity with such an injector, a dentist must exert a considerable force on the injector to eject the anesthetic from the cartridge through the needle of the injector and also must slowly effect the operation of the injection. For the purpose of solving such a problem, an electrically-driven dental injector has been proposed in recent years. Basically, the electrically-driven dental injector comprises a pinion which is rotated through a transmission gear mechanism by a motor with reduction gear, and a plunger rod having a rack meshed with the pinion. Forward or advance movement of the plunger rod causes a plunger rubber in the cartridge to push, thereby ejecting the injection liquid in the cartridge through a needle penetrated into a rubber plug which seals an end of the cartridge opposite the plunger rubber. In order to inject the injection liquid into the mouth cavity, the plunger rod is advanced at an extremely low speed. Upon completion of the operation of injection, it is required to retract the plunger rod from the advanced position, but if the retraction of the plunger rod should be effected with a reverse rotation of the motor with reduction gear, it would take too much time to return the plunger rod from it's advanced position to its initial position. In order to solve this problem, the operative connection between the plunger rod and its drive mechanism may be interrupted so that the plunger rod can be manually freely pushed back.

However, since there has heretofore been employed an arrangement for disengaging the pinion from the mesh with the rack to interrupt the operative connection between the plunger rod and the drive mechanism, it has been necessary for the dentist to manually operate an operating part from the exterior of the injector. It has been very troublesome to manually push back the plunger rod while operating the operating part each time. There has been strong needs for development of an electrically-driven dental injector wherein a plunger rod can be manually pushed back directly upon completion of the operation of injection without any manual operation of the injector.

DISCLOSURE OF THE INVENTION

An object of the invention is to provide an electrically-driven dental injector which can comply with such needs.

According to the present invention, there is provided an electrically-driven dental injector comprising a housing having a nose portion, a support member secured to said nose portion and having a forwardly protruding socket for receiving a barrel adapted to contain a cartridge therein, means for coupling the barrel with the socket, a plunger rod sidably mounted in a bore in the support member and movable between its initial position and it's forwardly advanced position to push a plunger rubber in the cartridge, the plunger rod having a rack, a pinion meshed with the rack to advance the plunger rod, an electrical motor with reduction gear mounted within the housing, a planetary reduction gear located between said motor and said pinion and housed in a casing, a latch mechanism for coupling a ring gear of the planetary reduction gear with the casing or uncoupling the ring gear from the casing to transmit drive rotation of the motor to said pinion or interrupt the transmission of the rotation between the motor and the pinion, and an operating rod extending through the support member and operatively cooperating with the latch mechanism, whereby when the plunger rod is manually pushed from it's advanced position toward its initial position, the latch mechanism is released and at the same time, said operating rod protrudes beyond the inner bottom surface of the socket, and when the barrel is coupled to the socket, it pushes back the operating rod barrel with an end face of the barrel to engage the latch mechanism.

In a preferred embodiment of the invention, the planetary reduction gear comprises a two stage planetary reduction gear including two planetary reduction gear units, the ring gear being of the first planetary reduction gear unit. The latch mechanism includes a plurality of latching grooves formed in the ring gear on its periphery with a lug defined between the two adjacent grooves, a steel latching ball located in an aperture in the peripheral wall of the casing and adapted to engage or disengage from the latching groove and a lever pivoted at its lower end to housing adjacent the casing, the forward end of the lever operatively cooperating with the operating rod. A length of said operating rod is such that the forward end of the operating rod is retracted to the inner bottom surface of the socket when it abuts and pushes the lever toward the latching ball to force it into the latching groove, thereby coupling the ring gear with the casing.

BEST MODE FOR CARRYING OUT THE INVENTION

Figure 6:
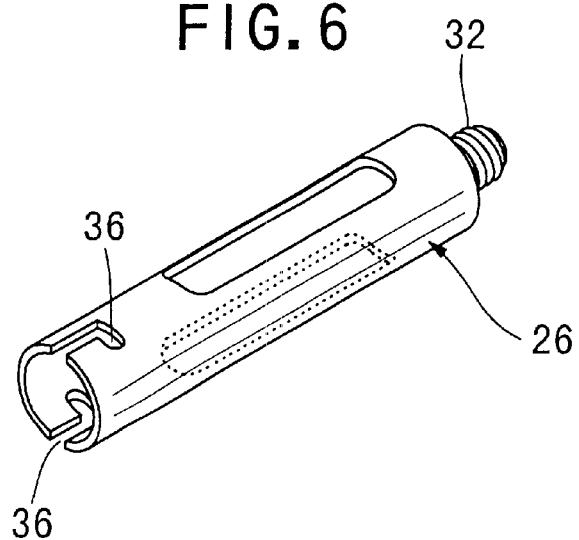
FIG. 6 is a perspective view of a barrel adapted to be coupled to a socket of the injector.

Referring to the drawings, and more particularly, to FIGS. 1, 3, 4 and 5 thereof, there is shown an electrically driven dental injector generally indicated at reference numeral 10, in accordance with the present invention, and having a housing 16 including a forwardly protruding nose portion 12 and a battery holder 14. The nose portion 12 of the housing 16 is formed from plastic material and is provided with a metallic support member 20 secured thereto and having a forwardly protruding socket 18 in the support member 20. A barrel 26 and is adapted to be inserted into and coupled to the socket 18, with a cartridge 24 filled with an injection liquid 22 such as an anesthetic received therein. As can be best seen in FIG. 6, the barrel 26 is provided at its forward end with a threaded portion 32 to which a needle fitting 30 with needles 28 is threadedly connected. Coupling of the barrel 26 with the socket 18 may be accomplished by engagement of diametrically opposite pins 34 protruding radially inwardly of the socket 18, with corresponding L-shaped slots 36 formed in the cylindrical wall of the barrel 26 at its open end.

Figure 1:
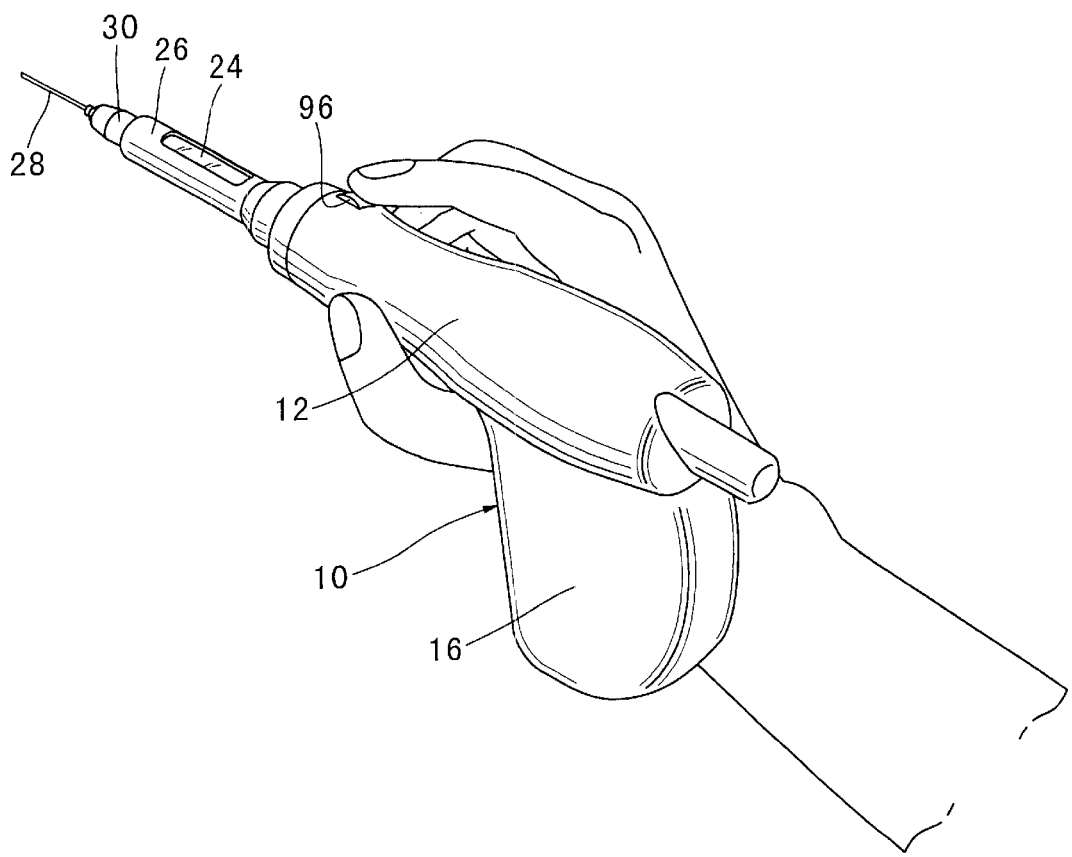
FIG. 1 is a perspective view of an electrically-driven dental injector constructed in accordance with the present invention.
Figure 2:
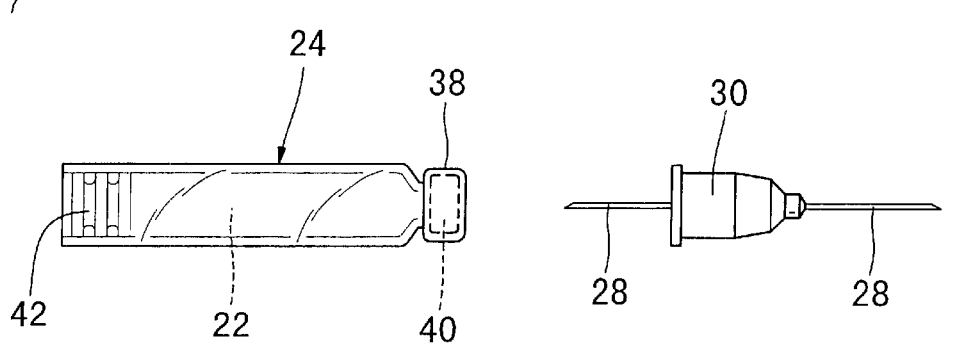
FIG. 2 is a cross-sectional view of a needle and a cartridge used in the electrically-driven dental injector according to the invention.
Figure 3:
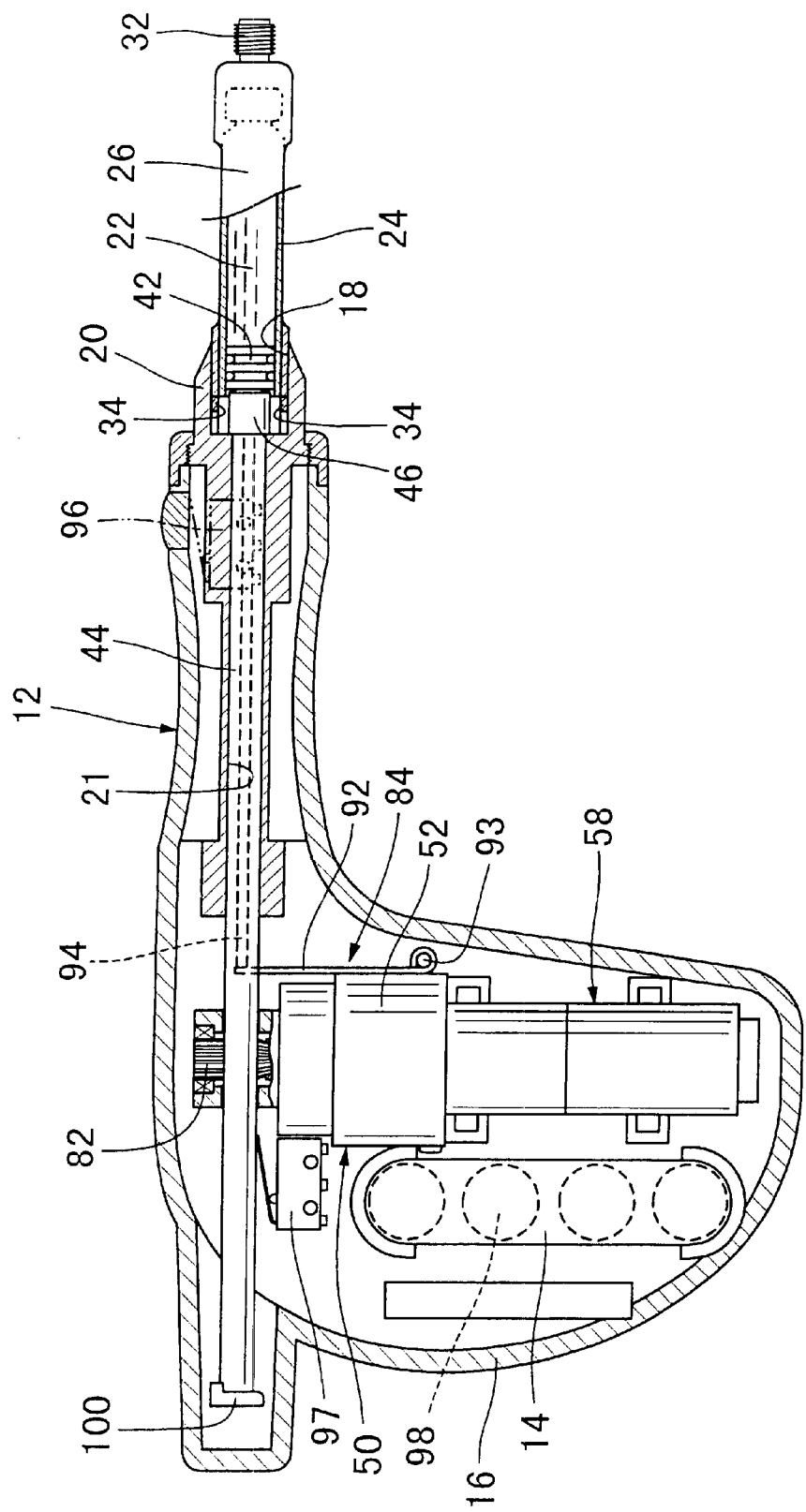
FIG. 3 is a cross-sectional view of the electrically-driven dental injector according to the invention.
Figure 4:
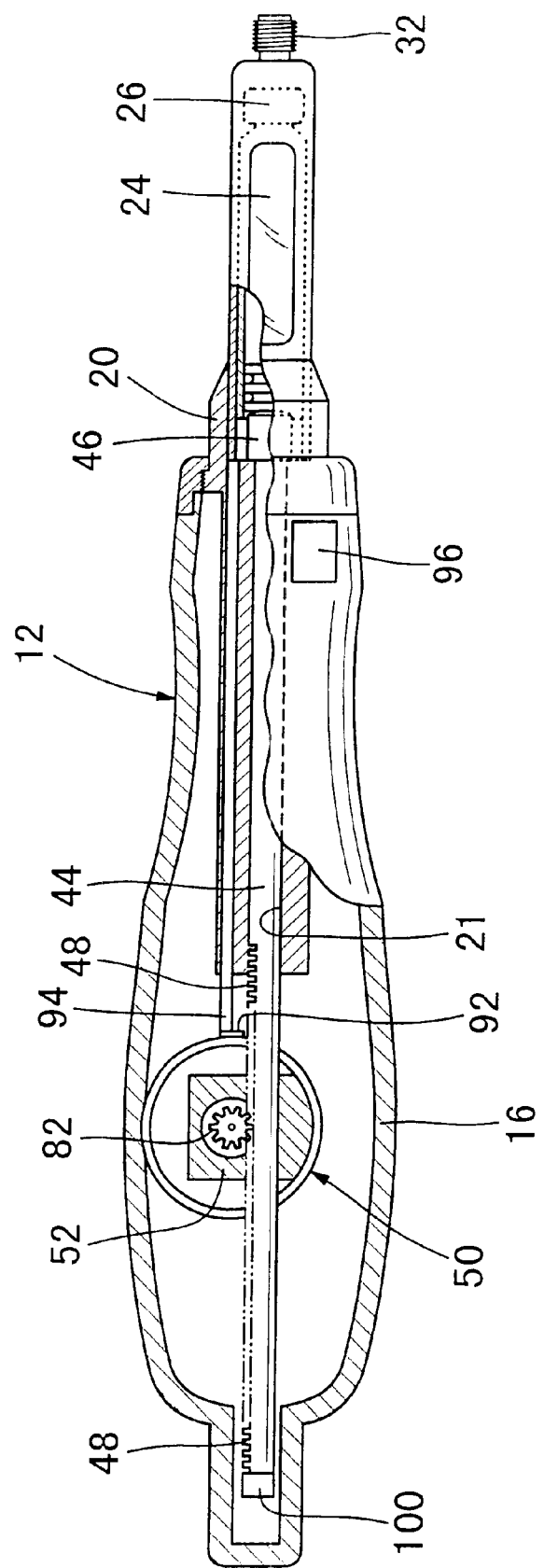
FIG. 4 is a top plan view in section of the electrically-driven dental injector according to the invention.
Figure 5:
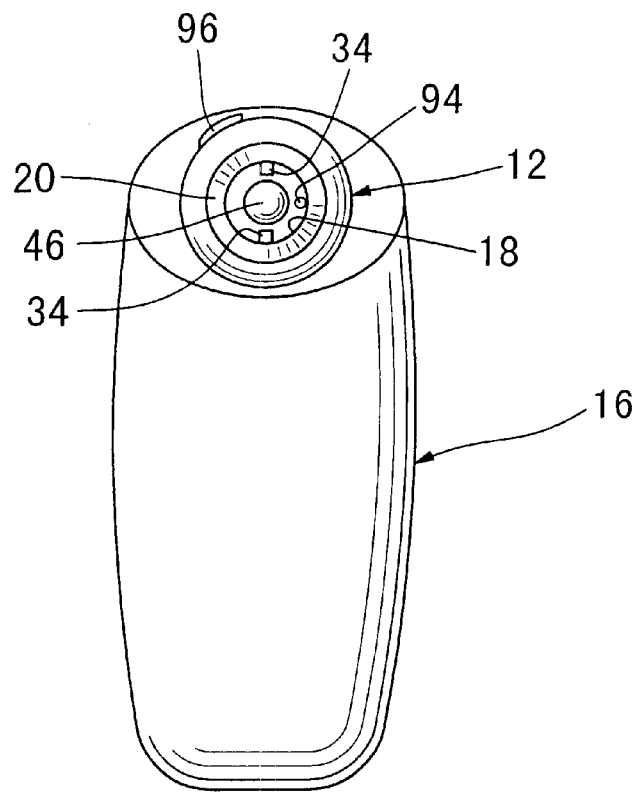
FIG. 5 is a front elevation view of the electrically-driven dental injector according to the invention.

As shown in FIG. 2, the cartridge 24 conventionally includes a rubber plug 40 retained at the end of the cartridge by a metallic cap 38 for sealing and adapted to be penetrated with the inner needle of the needle fitting 30 when it is attached to the barrel 26, and a plunger rubber 42 fitted in an open end of the cartridge.

Figure 7:
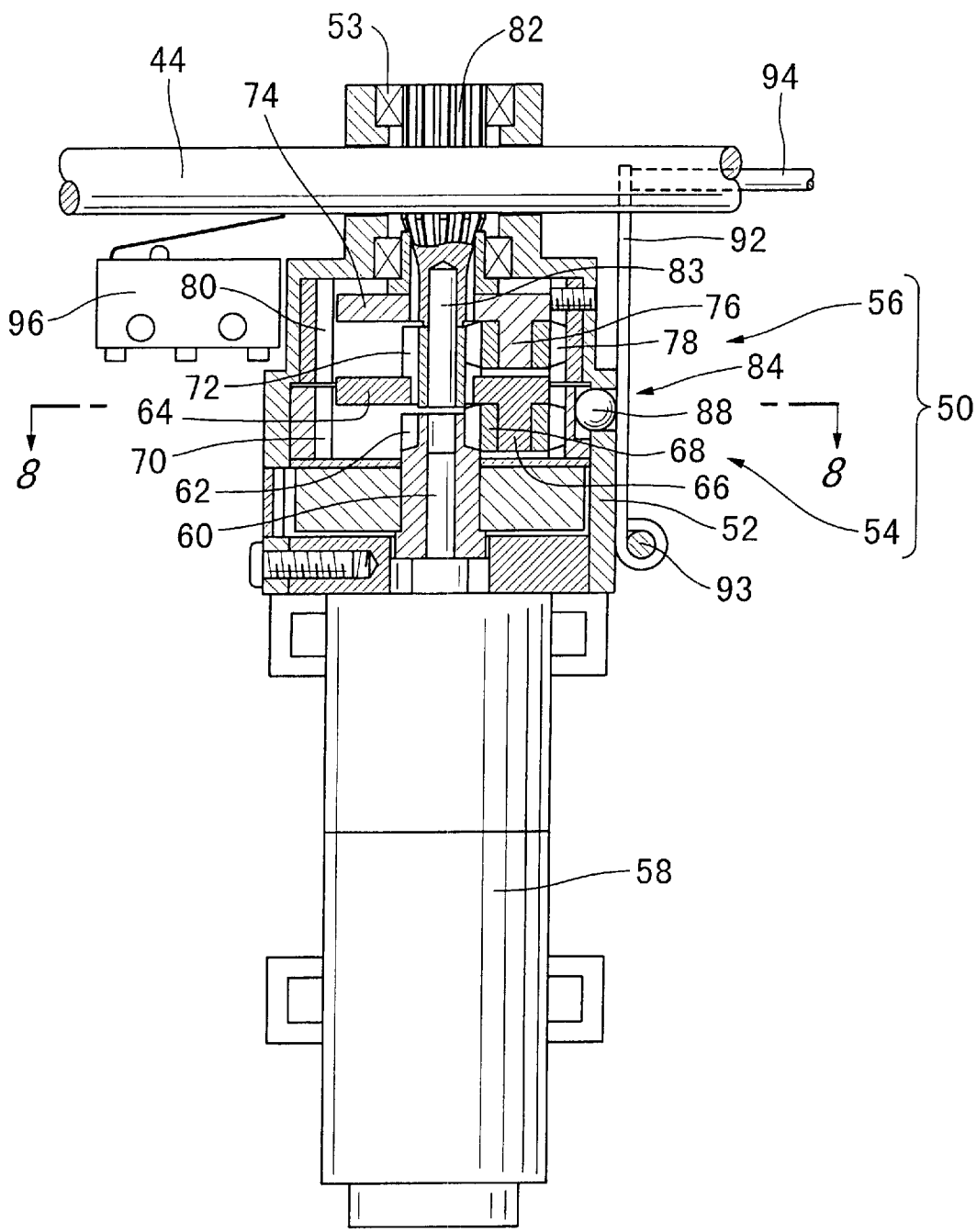
FIG. 7 is an enlarged cross-sectional view of a planetary reduction gear.
Figure 8:
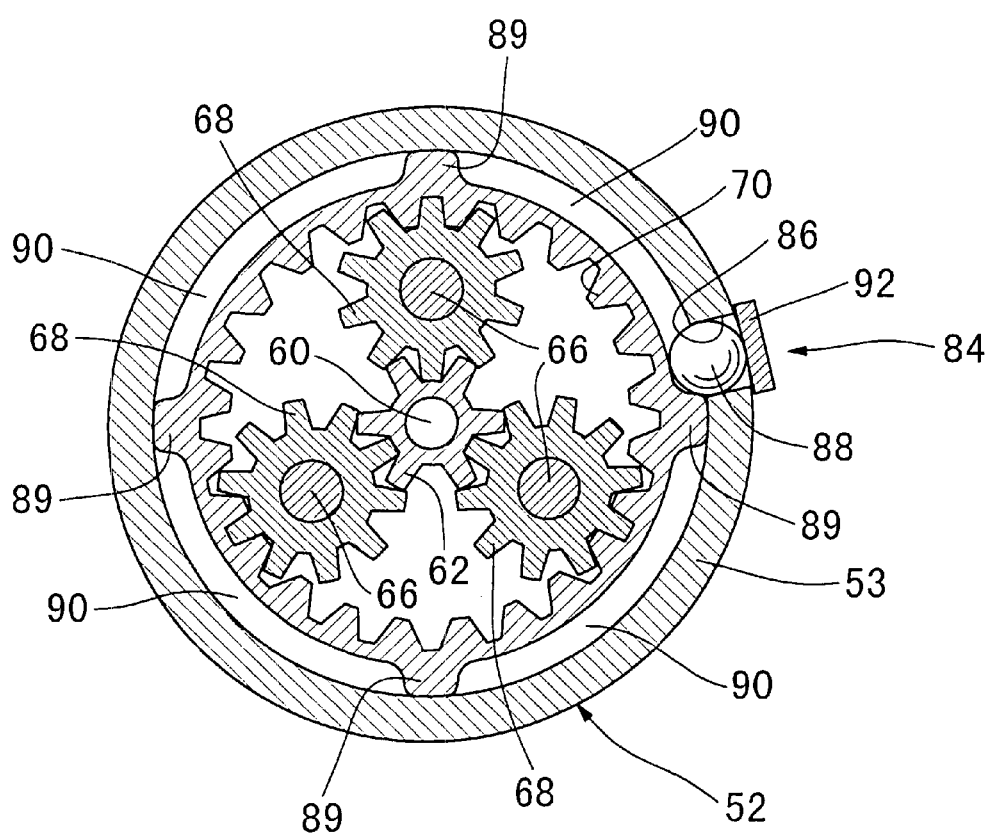
FIG. 8 is a top plan view in section of a first stage planetary reduction gear unit of the reduction gear, taken along line 8—8 of FIG. 7.

A metallic plunger rod 44 is mounted in a longitudinal bore 21 in the support member 20 for movement thereof between an advanced position and an initial position, and has an enlarged head 46 secured to the forward end thereof to define a tip thereof and adapted to abut and push the plunger rubber 42 of the cartridge 24. The plunger rod 44 is provided with rack 48 formed therein from the mid portion to the rearward end of the plunger rod (see FIG. 4) and extends through a casing 52 in which a planetary reduction gear 50 is housed (see FIG. 7). The rack 48 meshes with a pinion 82 rotatably mounted in bearings 53 in the casing 52 and driven through the planetary reduction gear 50 by an electric motor with a reduction gear, which is fixed to the housing 16. As can be best seen in FIGS. 7 and 8, the planetary reduction gear 50 includes planetary reduction gear units 54 and 56 to define a two-stage reduction gear which results in an increase in reduction ratio. The first stage-planetary reduction gear unit 54 includes a sun gear 62 fixed to an output shaft 60 of the motor 58, and planetary gears 68 each rotatably mounted on a support shaft 66 fixedly secured to a disk 64 and meshing with the sun gear 62. The planetary gears 68 mesh with a ring gear 70 disposed in the casing 52. The second stage-planetary reduction gear unit 56 has a sun gear 72 rotatably mounted on a support pin 83 press fitted in a hub of the pinion 82. The disk 64 is splined to the sun gear for rotation together with it. The second stage-planetary reduction gear unit 56 also has planetary gears 78 meshing with the sun gear 72 and each rotatably mounted on a support shaft 76 fixedly secured to a disk 74 which in turn is splined to s hub of the pinion 82 for rotation together with it. The planetary gears 78 mesh with a ring gear 80 disposed in and fixed to the casing 52.

There is provided a latch mechanism 84 movable between an engagement position in which the ring gear 70 the first stage-planetary reduction gear unit 54 of the planetary reduction gear 50 is coupled to casing 52 and release position in which the ring gear 70 is uncoupled from the casing 52 to transmit rotative drive from the output shaft 60 of the motor 58 with reduction gear to the pinion 82 and to interrupt transmission of the rotative drive between the motor 58 and pinion 82. The latch mechanism 84 includes a plurality of latching grooves 90 formed in the ring gear 70 on its periphery with a lug 68 defined between the two adjacent grooves 90, a steel latching ball 88 located in an aperture 86 in the peripheral wall 53 of the casing 52, and a lever 92 pivoted at its lower end to housing 16 adjacent the casing 52 as indicated at reference numeral 93, and operable to permit the latching ball 88 to selectively engage and disengage from the latching groove 90. The lever 92 operatively cooperates at its upper end with an operating rod 94 extending longitudinally through the support member 20. A length of the operating rod 94 is such that the forward end of the operating rod 94 is retracted to the inner bottom surface of the socket 18 when it abuts and pushes the lever 92 toward the latching ball 88 to force it into the latching groove 90, thereby coupling the ring gear 70 to the casing 52.

Assuming that the barrel 26 has been removed from the socket 18 and the plunger rod 44 is in the most advanced position, the pinion 82 is rotated through the rack 66 by manually pushing the plunger rod 44 so that a torque will be applied through the disk and sun gear of the second stage-planetary reduction gear unit 56, and the planetary gears of the first stage-planetary reduction gear unit 54 to the ring gear 70. The rotation of the ring gear 70 causes the lug 89 to push the latching ball 88 out of the latching groove 90, thereby releasing the coupling of the ring gear 70 with the casing 52. Thus, the rotation of the pinion 82 due to retraction of the plunger rod 44 causes the sun gear 72 of the second stage-planetary reduction gear unit to rotate, thereby merely rotating the first stage-planetary reduction gear unit 54 along with the ring gear 70 around the sun gear 62. For this reason, a dentist can freely push back the plunger rod 44. When the latching ball 88 is forced out of the latching groove 90, the lever 92 is pivoted forwardly or clockwise about the pivot point 93 to push forwardly the operating rod 94. At this point, the forward end of the operating rod 94 protrudes forwardly beyond the inner bottom surface of the socket 18.

There is provided an operating switch 96 at the top surface of the nose portion 12 of the housing 16, and a limit switch 97 is provided in the housing 16 for defining a stroke of the plunger rod 44. A plurality of batteries 98 are held in the buttery holder 14 as a power source for the motor 58.

With the cartridge 24 inserted in the barrel 26, the latter is inserted into the socket 18 and then, turned relative to it so that the pins 34 can be engaged in the L-shaped slots 36 in the barrel 26 for coupling between them. At the same time, the end face of the barrel 26 abuts and pushes back the operating rod 94. The rearward shift of the operating rod 94 causes the lever 92 to be pivoted rearwardly or counter-clockwise about the pivot point 93, thereby pushing the latching ball 88 in the latching groove 90. This state is maintained as long as the barrel 26 is coupled to the socket 18. The needle fitting 30 is threadedly connected to the threaded portion 32 so that the inner needle pierces the rubber plug 40 of the cartridge 24 for communication with injection liquid in the cartridge.

The nose portion 12 of the housing 16 is held in the dentist's hand and the motor 58 with reduction gear is actuated by depressing the operating switch 96 with the forefinger to rotate the sun gear 62 on the output shaft thereof. The planetary gears 68 revolves around the rotating sun gear 62 due to the fact that the ring gear 70 has been coupled to the casing 52. This results in rotation of the disk 64 and hence, the sun gear 72 of the second stage-planetary reduction gear unit so that the planetary gears 78 revolves around the rotating sun gear 72. Thus, the disk 74 and hence, pinion 82 rotate and due to the rack 48 meshing with the pinion 82, the plunger rod 44 is moved linearly to advance the plunger rubber 42 in the cartridge 24, thereby ejecting through the outer needle the injection liquid in the cartridge 24. The operation of injection continues until an operating piece 100 which secured at the rearward end of the plunger rod 44, operates the limit switch 97 to unactuate the motor 58.

When the operation of injection has been completed, the needle fitting 30 is removed from the barrel 26 and then, the barrel 26 is uncoupled from the socket 18 so that the empty cartridge 24 can be removed from the barrel 26. In this state, the plunger rod 44 protrudes forwardly only for its stroke. Thus, the plunger rod 44 can be freely moved rearwardly by pushing it due to the reason as described above. At this point, the lever 92 is pivoted clockwise by means of the latching ball 88 which is forced out of the latching groove 90 and the pivotal movement of the lever 92 causes the operating rod 94 to be pushed forwardly, thereby protruding its forward end beyond the inner bottom surface of the socket It will be understood from the foregoing that the plunger rod can be released from interconnection with the drive source merely by manually pushing back the plunger rod from it's advanced position upon completion of injection so that it can be freely moved to its initial or retracted position, and if the barrel is loaded in the socket, the plunger rod can be automatically operatively connected to the drive source. Thus, the electrically-driven dental injector according to the invention is easy to operate.

What is claimed is:

1. An electrically-driven dental injector comprising a housing having a nose portion, a support member secured to said nose portion and having a forwardly protruding socket for receiving a barrel adapted to contain a cartridge therein, means for coupling said barrel with said socket, a plunger rod sidably mounted in a bore in said support member and movable between its initial position and it's forwardly advanced position to push a plunger rubber in the cartridge, said plunger rod having a rack, a pinion meshed with said rack to advance said plunger rod, an electrical motor with reduction gear mounted within said housing, a planetary reduction gear located between said motor and said pinion and housed in a casing, a latch mechanism for coupling a ring gear of said planetary reduction gear with said casing or uncoupling said ring gear from said casing to transmit drive rotation of the motor to said pinion or interrupt the transmission of the rotation between said motor and said pinion, and an operating rod extending through said support member and operatively cooperating with said latch mechanism, whereby when said plunger rod is manually pushed from it's advanced position toward its initial position, said latch mechanism is released and at the same time, said operating rod protrudes beyond the inner bottom surface of the socket, and when said barrel is coupled to said socket, it pushes back said operating rod barrel with an end face of the barrel to engage said latch mechanism.

2. An electrically-driven dental injector according to claim 1, wherein said planetary reduction gear comprises a two stage planetary reduction gear including two planetary reduction gear units, said ring gear being of said first planetary reduction gear unit.

3. An electrically-driven dental injector according to claim 1, wherein said latch mechanism includes a plurality of latching grooves formed in the ring gear on its periphery with a lug defined between the two adjacent grooves, a steel latching ball located in an aperture in the peripheral wall of the casing and adapted to engage or disengage from said latching groove and a lever pivoted at its lower end to housing adjacent the casing, the forward end of said lever operatively cooperating with said operating rod.

4. An electrically-driven dental injector according to claim 3, wherein a length of said operating rod is such that the forward end of the operating rod is retracted to the inner bottom surface of said socket when it abuts and pushes the lever toward the latching ball to force it into the latching groove, thereby coupling the ring gear with the casing.

* * * * *